United States Patent [19]

Glassman

[11] Patent Number: 4,524,767

[45] Date of Patent: Jun. 25, 1985

[54] SURGICAL DRAPES

[76] Inventor: Jacob A. Glassman, 1680 Michigan Ave., Miami Beach, Fla. 33139

[21] Appl. No.: 395,803

[22] Filed: Jul. 6, 1982

[51] Int. Cl.³ ............................................ A61F 13/00
[52] U.S. Cl. ................................................ 128/132 D
[58] Field of Search .............. 128/132 D, 132 R, 155, 128/156

[56] References Cited

U.S. PATENT DOCUMENTS

| | | | |
|---|---|---|---|
| 3,721,234 | 3/1973 | Hadtke et al. | 128/132 D |
| 3,826,253 | 7/1974 | Larsh et al. | 128/132 D |
| 3,882,859 | 5/1975 | Ericson | 128/132 D |
| 4,027,665 | 6/1977 | Scrivens | 128/132 D |
| 4,323,062 | 4/1982 | Canty | 128/132 D |

Primary Examiner—Henry J. Recla
Assistant Examiner—Karin M. Reichle
Attorney, Agent, or Firm—Elmer L. Zwickel

[57] ABSTRACT

A surgical drape provided with a multiple sided incise drape in its surgical area that is separately attached to the surgical drape after it is arranged over the surgical area and is surrounded by a number of flaps or absorbent towels that may be utilized also to reduce the effective size and shape of the surgical area. Modifications of these surgical drapes are the provision of a surgical drape including a pre-attached incise drape and a drape designed for use for limb surgery or amputations having absorbent flaps strategically arranged around an incise drape that is wrapped around and adhered to the critical area of the limb.

5 Claims, 14 Drawing Figures

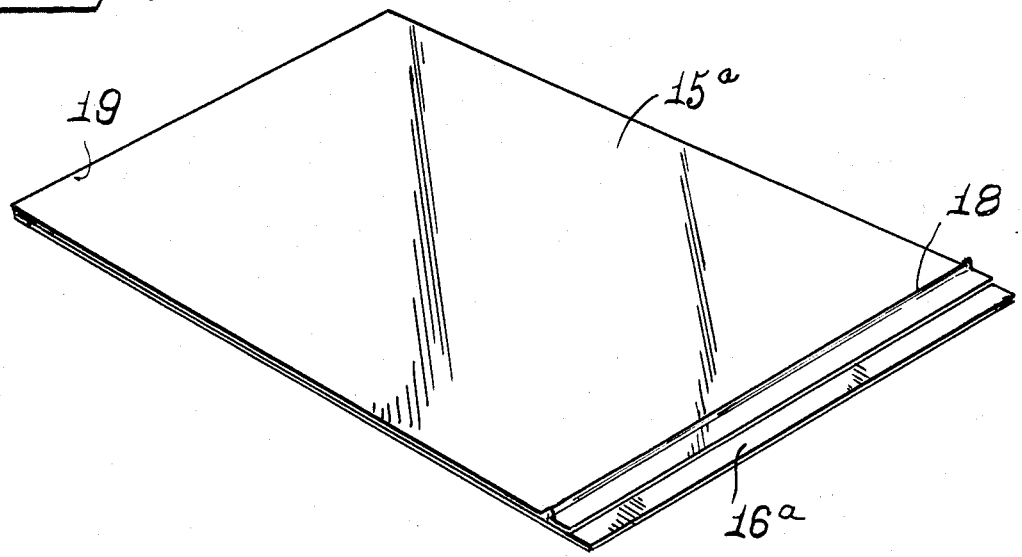
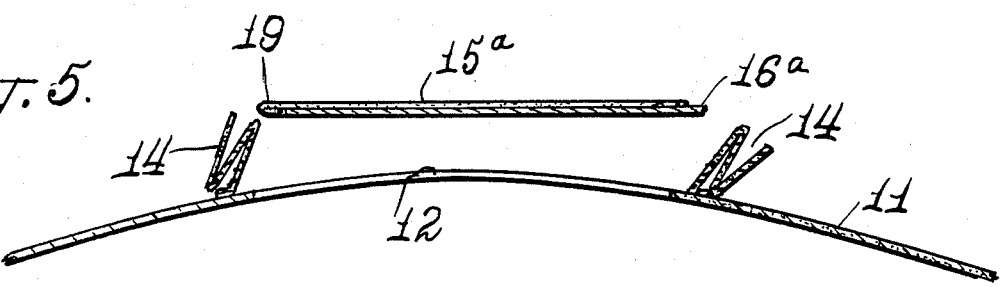
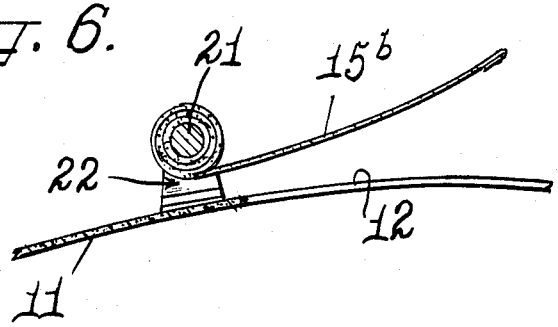
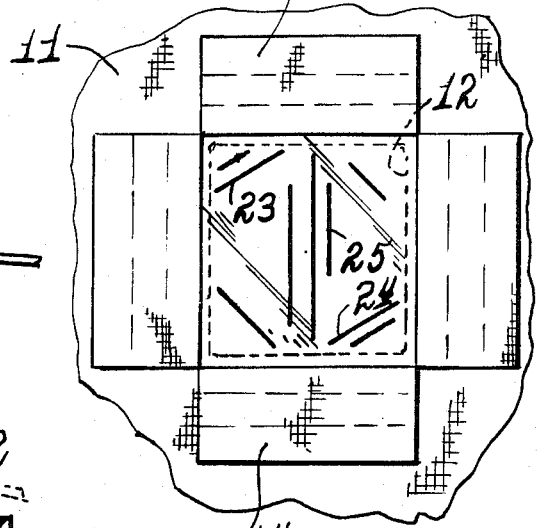
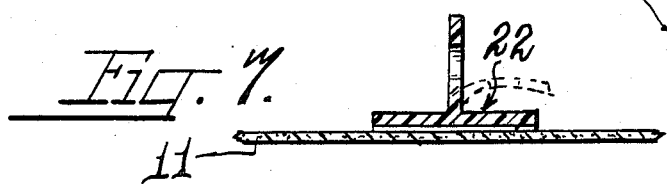

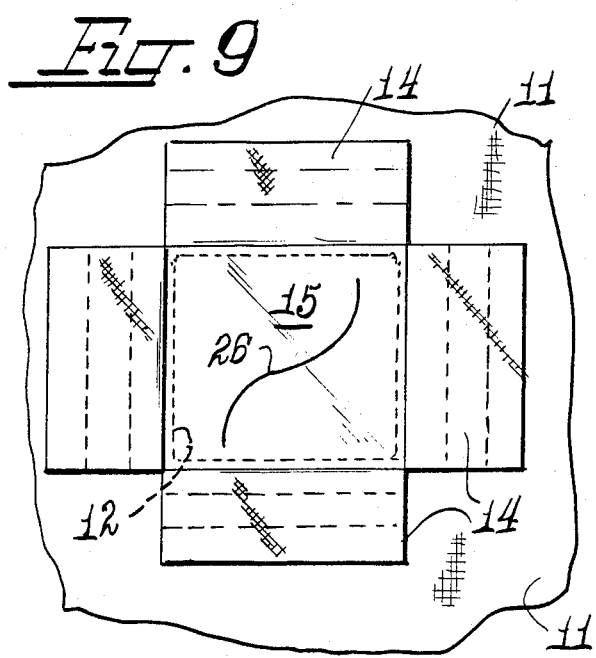
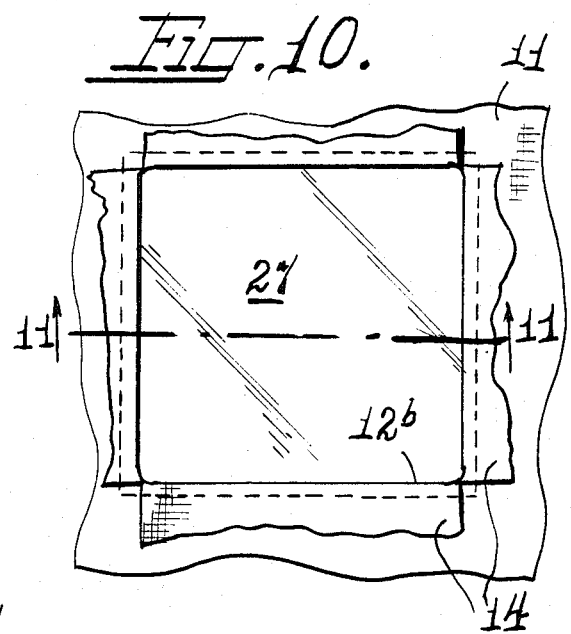
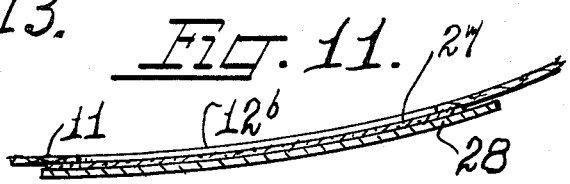
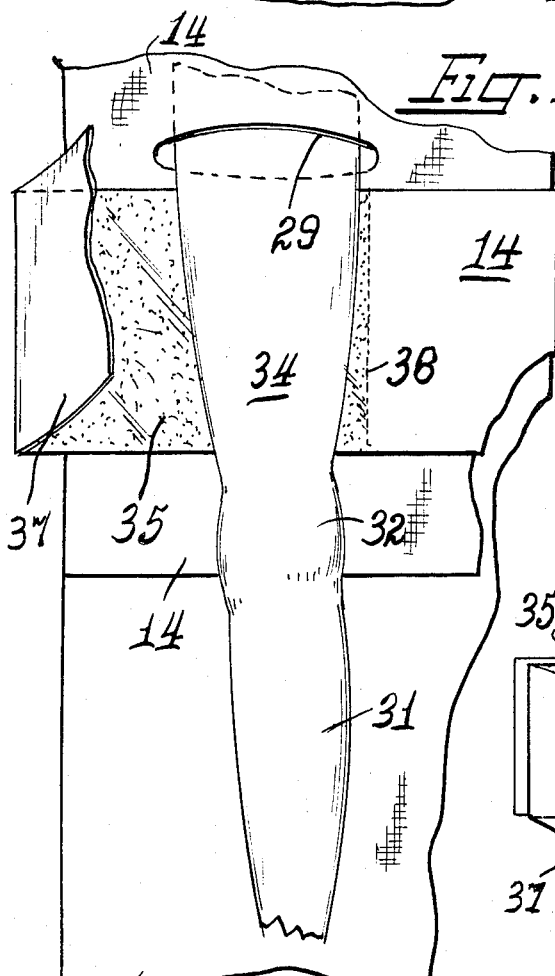
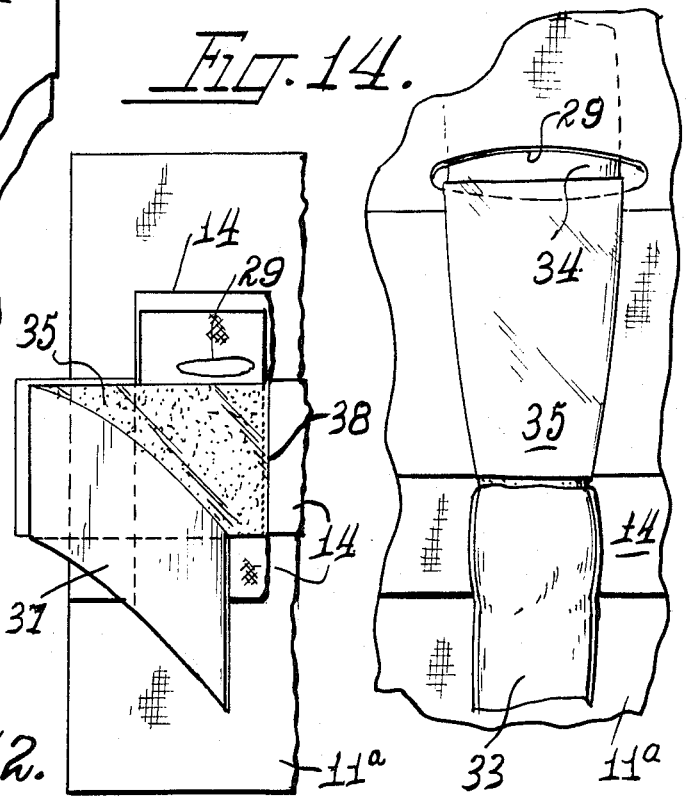

SURGICAL DRAPES

The invention relates to improvements in Surgical Drapes and particularly to such main drapes as are fabricated from non-woven absorbent and non-absorbent disposable material shaped and sized to adapt them to various surgical needs. Some such drapes are formed with an operative opening or slit affording access for the surgeon to cut into the skin of an underlying patient. Such an opening is usually square or rectangular in shape or perhaps oval or slit-like and of small size. Frequently, the opening is manually cut by the surgeon or his assistant to enlarge same or to vary its shape or size depending upon the specific needs of the surgeon. There are also times when even a specially pre-cut opening has to be re-shaped and/or varied in size to meet specific requirements. In addition to the foregoing specifics of a main or surgical drape, a transparent incise drape is always associated with it. In one form the incise drape is laid over the skin of the abdomen just prior to placing the surgical drape. The incise drape adheres to the prepared or antiseptically painted skin and the main or surgical drape is not adhered to the underlying incise drape and is free to slide relative thereto. Some commercially acceptable incise drapes are impregnated or otherwise chemically treated to create an anti-bacterial defense against living organisms that may still be present in or on the skin surface even after the surface has been scrubbed with soap and swabbed with an iodinated preparation.

Following such lengthy preparation for surgery, the surgeon may proceed, initially by making an incision at the exact desired site, knowing that the sterile transparent incise drape will remain snugly cemented to the skin of the patient. Because of the incise drape, the surgeon need never handle the bare skin or unintentionally "paw" it hundreds of times during the operative procedure which would squeeze out remaining bacteria from the deep crypts of the skin, and thus contaminate the operative wound.

Another form of surgical drape is one intended for limb operations or amputations. This type has the incise drape affixed to the main drape and after the incise drape is wrapped around the operative area of the limb it is separated from the main drape so that the limb is free to be moved during surgery.

The improved surgical drapes herein disclosed retain all the advantages of known main drape structures discussed above and is particularly concerned with the combination of a surgical drape and an integral incise drape; and to a novel incise drape per se. The herein disclosed items are less costly to produce and less cumbersome to use, when combined. More specifically, the new surgical drapes and incise drapes have the skin contacting surface coated with a pressure sensitive adhesive as before, and the incise drape may be rolled or folded in such manner that it may be unfolded or unrolled from a position preferably above the cut-out opening in the main drape. The incise drape of such size as to completely overly and extend beyond the edges of any size operative opening regardless of how large. Also, the incise drape may be provided with a select reinforced edge or edges so as to enable one to stretch and set the incise drape in place over the skin without wrinkling. Further, the disclosed incise drapes eliminate the waste of using an unduly large piece of expensive material and excessive manpower to place it over the patient's abdomen. The time factor is also considerably reduced because the surgeon or his assistant can handle the whole procedure alone.

As to the disclosed surgical drapes per se; the operative area of each is surrounded with integral flaps which when folded down over a large operative area, reduces and varies its effective size and shape. Also such flaps serve to absorb the blood and secretions surrounding the incision.

In use of earlier structures the soft absorbent or non-absorbent main surgical drape is arranged over the surgical patient. Such drapes have a small operative opening which usually has to be enlarged and reshaped by cutting away drape material by the surgeon or his assistant. Prior to positioning such surgical drape over the body, a transparent plastic adhesive incise drape is laid over the skin of the operative area. The incise drape has a pressure adhesive on its bottom surface and, in application, the drape is held tautly by two persons grasping the drape at opposite edges and slowly lowering it to contact the body in such manner as to avoid the presence of wrinkles. The foregoing procedure is expensive in that an excessively large piece of incise material is required to assure covering the entire exposed skin; excessive time is required to arrange the incise drape properly, and additional time is consumed in cutting and re-arranging the non-adherent slippery shifting of the operative opening in the main drape.

In the present disclosure of an incise-main drape combination, the main drape is formed with a relatively large operative opening covering a wide abdominal or thoracic area having integral with one or more of its edges, a pre-folded absorbent towel. The pre-folded towels or absorbent flaps may be infolded over the operative opening to reduce it to a required size and shape. In this manner the time consuming prior practice of cutting and enlarging the opening is avoided.

Now, prior to unfolding the pre-folded towels or absorbent flaps, a piece of incise material, constituting an incise drape, is applied directly to the skin over the entire operative area. Preferably, the incise drape is attached to the main drape along one edge of the operative opening. In either event, only one person is required to arrange the incise drape over the operative area and secure it adhesively to the patient. Hence, considerable man-power is saved by this simple procedure. Further, the saving of incise-drape material is considerable because the incise drape need not be excessively large as heretofore required.

The herein disclosed amputation drape is comprised of a regular non-woven main drape having an opening through which the limb (such as a leg) is passed after which the thigh is wrapped in an incise type drape. This allows for free movements of the thigh which are necessary for successful surgery.

The foregoing and other advantages of the invention will become apparent with reference to the following descriptions and accompanying drawings, in which:

FIG. 4 is a perspective view of an unattached incise-drape prior to removal of its backing.

FIG. 5 is a view similar to FIG. 2, showing the placement of the FIG. 4 incise-drape within an operative opening in a surgical drape.

FIG. 6 is another sectional view of a surgical drape having pre-folded flaps or towels for varying the size and/or shape of the operative opening, fitted on one edge of the incise opening with a rolled incise drape, shown partially unrolled for application.

FIG. 7 is a sectional detail view of one of the brackets shown in FIG. 6, illustrating the flexibility of same.

FIG. 8 is a fragmentary plan view of a main drape having an incise drape associated with its operative opening, indicating generally, the location of various abdominal incisions and the relationship of the selectively foldable absorbent flaps or towels around the site of the surgical incision.

FIG. 9 is a view similar to FIG. 8, indicating the location of Thoracic incision and Thoraco-Abdominal incision.

FIG. 10 is a plan view of the operational area of a main drape showing an integrally attached incision drape.

FIG. 11 is a sectional view of the FIG. 10 drape, taken substantially on line 11—11 of FIG. 10.

FIG. 12 is a plan view of an incision-main drape combination of a character utilized most generally for limb operations or amputations.

FIG. 13 illustrates the drape assembly associated with a limb to be operated on or amputated, prior to total sterile coverage.

FIG. 14 is a view similar to FIG. 13, showing the sterile covering on the limb.

Figure 1:
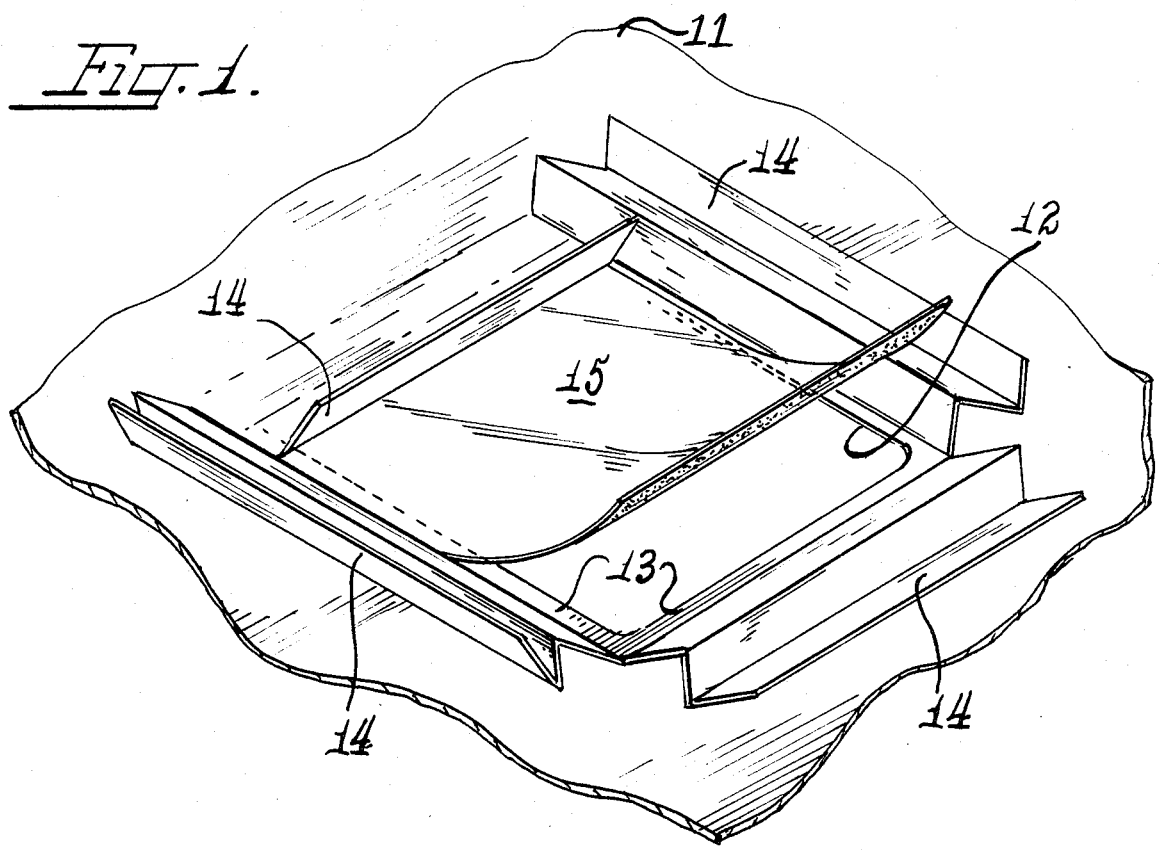
FIG. 1 is a perspective view of the operative area of a surgical abdominal drape illustrating the presence of an integral transparent incise-drape, and attached pre-folded towels or flaps around the perimeter of the operative opening.
Figure 2:
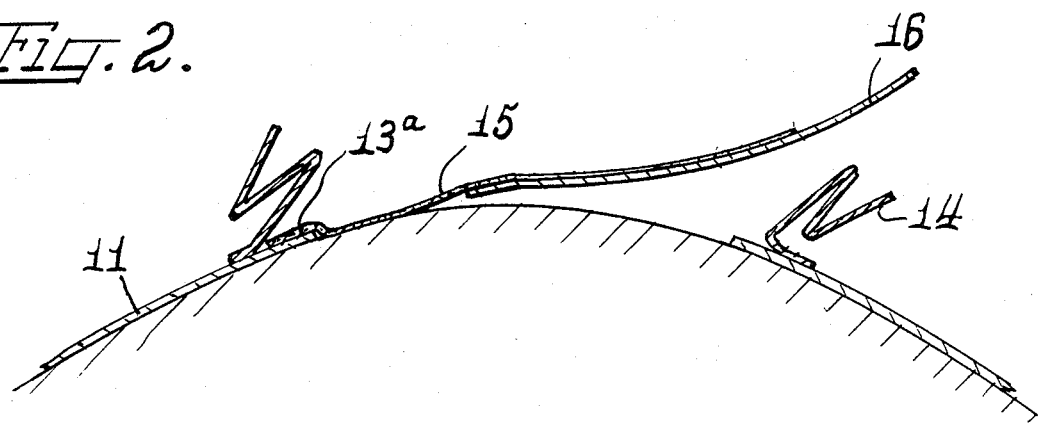
FIG. 2 is a sectional view of the operative area taken substantially on line 2—2 of FIG. 1, showing the placement of the attached transparent incise-drape.
Figure 3:
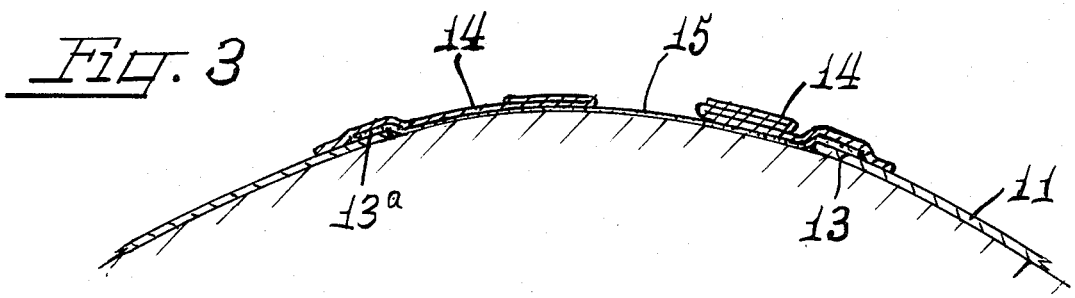
FIG. 3 is a view similar to FIG. 2, showing the incise-drape adhesively secured to the patient's skin and the pre-folded towels or flaps partially overlying the incise-drape so as to reduce the size of the operative opening.

Now, referring to the embodiment of the invention as disclosed in FIGS. 1 to 3, the main-drape 11 is provided with an operative opening 12 that is much larger than operative openings heretofore found in present known main drapes. Each margin 13 of said opening is fitted with an integral in-folded absorbent flap or towel 14. This pre-folded flap or towel is spaced from the free edge of the margin 13 for the purpose to be made known presently. Pre-folding of each absorbent towel or flap 14 is preferred so as to have all or a portion of its width carried inwardly to overlie a part of the operative opening 12 to reduce its size and/or shape.

Also, one margin 13 of the operative opening has, permanently attached thereto, as at 13a one edge of an adhesively coated transparent incise-drape 15. This incise-drape is of such size that when laid over the operative opening 12, as will be explained, its peripheral margins will overlie the remaining marginal edges 13 of opening 12. Thus, upon referring to FIG. 2, it will be observed that when a peel-off sheet 16 carried on the adhesive coated face of the incise-drape is withdrawn (FIG. 2) and the drape pressed downwardly, the adhesive will attach the incise drape securely to margins 13 of the main drape and also firmly to the underlying exposed skin of the patient.

After the incise drape is in place, all or any portion of any or most of the pre-folded towels or flaps 14 may be laid over the incise-drape to produce an operative opening of the required size and/or shape. The bottom faces of flaps 14 may carry an adhesive to fix their adjusted position over the incise-drape and prevent their displacement.

It should be quite evident that the foregoing structure and assembly will save much time and labor in re-shaping the operative opening 12 in the main-drape. Also, only one person will be required to stretch and apply the incise-drape 15 since one edge of same is securely attached to the main-drape (FIG. 2). While the incise-drape is being laid over opening 12, the incise-drape will have its adhesive covering sheet 16 slowly drawn from underneath it while at the same time the incise-drape 15 is pressed into contact with the surface of the skin.

The incise-drape 15a illustrated in FIGS. 4 and 5, is of the type that may be used in connection with the FIGS. 1-3 structure, or it may be used as a separate attachment. Specifically, the incise-drape 15a has a stiffening member adjacent one edge, such as a rib 18. When the sheet is to be applied over an operative opening, one margin 19, which may be reinforced by folding over its edge, is engaged to hold the sheet while the adhesive protective sheet 16a is withdrawn gradually. Then, while continuing to withdraw the protective sheet 16a the operator will grasp the free reinforced edge 18 of the incise-drape and hold it taut as it comes into contact with the skin.

FIGS. 6 and 7 show an incise-drape 15b entirely contained on roller rod 21. Here the rod ends are seated in folding brackets 22 (one shown) that are adhesively secured to the main drape 11 and infolded after the main drape is in place on the patient. Only one person is required to unroll the incise-drape and secure it over the operative site.

FIG. 8 is representative of the most common patterns 23, 24, 25, of incisions made for various types of abdominal surgery. As shown, the incision patterns lie within the confines of the operative opening 12 in the main drape 11, which opening is surrounded by a number of integrally attached foldable absorbent towels or flaps 14, any one or more of which may be infolded to alter the size and/or shape of the elective operative opening 12 in the drape.

In FIG. 9, which is similar to FIG. 8, a different kind of incision pattern 26 is illustrated. Such pattern is commonly known as a Thoracic incision or a Thoraco Abdominal incision. It should be understood that the operative opening 12 in both the FIG. 8 and the FIG. 9 disclosures is of sufficient size to accomodate whatever size and style of incision as is required to meet the needs of the operating surgeon. Irrespective of the incision's size or shape, it lies entirely within the confines of the operative opening 12 and is subsequently covered by an incise-drape 15.

The main drape 11 illustrated in FIGS. 10 and 11, has an operative opening 12b within which a transparent incise-drape 27 is secured around its margin to the bottom surface of the main drape within the operative opening. As best illustrated in FIG. 11, the bottom face of the incise-drape is adhesively coated and normally is protected by a sheet 28 that is peeled off at the time the drape is fitted over a patient so that the incise-drape can be adhered to the patient's skin.

The assembly shown in FIGS. 12, 13 and 14, is an abdominal and thoracic type of drape especially designed for operations on limbs and for amputation procedure. As shown, the main drape 11a which is of non-woven absorbent or non-absorbent materials, is of sufficient size to be placed beneath the limb to be operated upon or amputated. Consequently, the drape has no operative opening but instead has a transverse opening or slot 29 through which the entire limb (in this instance, a leg) is thrust. Following this, the foot (not shown), leg and knee (31 and 32 respectively) are sterilly wrapped (33) so as to be excluded from the operative field, leaving only the thigh 34 exposed.

A sterile incise drape 35 (FIG. 12) attached at one edge 38 to the main drape, and having its adhesive coated surface facing upwardly, has its protective sheet 37 peeled off and the incise drape 35 is then carried up over and adhesively secured ground and to the thigh (FIG. 14), thus securely and sterilly enclosing the thigh. As before, there are a number of flaps of absorbent towels 14 secured to the main drape 11a in the area surrounding at least three sides of the thigh. Once secured to the thigh, the incise drape is separated from the main drape along line 38 so that the leg can be moved about to the extent necessary to perform the required surgery.

While specific embodiments of the invention have been shown and described in detail to illustrate the application of the invention and its principles, it will be understood that the invention may be embodied in other manners without departing from the principles herein disclosed.

I claim:

1. A surgical drape comprising a main drape having a multiple sided operative opening adapted to be arranged over the surgical area of a patient, a number of absorbent accordion folded flaps integrally attached to the main drape along one of their marginal edges one outwardly of each peripheral margin of the operative opening, an incise drape being sized and shaped to lie over the operative opening and areas of the main drape inwardly of the folded flaps surrounding the operative opening, said incise drape having one edge attached to one of said peripheral margins, an adhesive covering the surface of the unsecured portion of said incise drape facing the operative opening and said peripheral margins, a removable sheet normally covering said adhesive coated surface whereby when said main drape is placed over said surgical area, said sheet is removable to expose the adhesivly coated surface and enable the incise drape to be adhesively secured to the remaining areas of the main drape inwardly of the flaps and to the surgical area of the patient within said operative opening, and said absorbent flaps being extendable to overlie at least a portion of the incise drape disposed over the operative opening.

2. A surgical drape comprising a main drape adapted to be spread over the body of a patient, said drape having a multiple sided operative opening therein adapted to overlie the surgical area of the patient, an incise drape being sized and shaped to lie over said operative opening and the margins thereof, an adhesive covering the surface of said incise drape facing the operative opening, said incise drape being adhesively secured in place along one of its marginal edges to one of the margins of the opening in the surgical drape, a removable sheet of material normally covering the adhesive on the unsecured portion of the incise drape, whereby after the main drape is placed over said surgical area, said sheet is removable to expose the adhesively coated surface and permit adhesive securement of the incise drape to the surgical area of the patient within said operative opening and to the remaining margins of the opening.

3. A surgical drape comprising a main drape adapted to overlie a substantial portion of a body of a patient, said drape having an opening therein adapted to be located over an operative area of the body, an incise drape being sized and shaped to overlie said operative opening and the peripheral margins of said opening, and an adhesive on the surface of the incise drape facing the operative opening, a removable covering sheet overlying the entire adhesive surface of the incise drape, whereby after the main drape is placed over the surgical area, said sheet is removable to expose the adhesive and enable adhesive securement of the margins of the incise drape to the peripheral margins of said opening and to the operative area of the patient within said operative opening.

4. The surgical drape recited in claim 3, wherein at least one inwardly foldable absorbent flap is secured to the drape and is spaced from the peripheral margins of the opening, said flap being adapted to overlie at least a portion of the underlying incise drape when unfolded and placed thereover.

5. The surgical drape recited in claim 4 wherein inwardly foldable absorbent flaps are provided outwardly of the peripheral margins of the operative opening.

* * * * *